United States Patent [19]
Seminoff et al.

[11] Patent Number: 5,126,146
[45] Date of Patent: Jun. 30, 1992

[54] CELLULOSIC COATING

[75] Inventors: Leah A. Seminoff; Gaylen M. Zentner, both of Lawrence, Kans.

[73] Assignee: Merck & Co., Inc., Rahway, N.J.

[21] Appl. No.: 425,619

[22] Filed: Oct. 23, 1989

[51] Int. Cl.$^5$ .................................................. A61K 9/24
[52] U.S. Cl. .................... 424/973; 424/468; 106/186; 106/162
[58] Field of Search ................ 424/468, 473; 106/162, 106/182

[56] References Cited

U.S. PATENT DOCUMENTS 4,931,285  6/1990  Edgren et al. ...................... 424/468

OTHER PUBLICATIONS

Bindschaedler et al., J. Controlled Release 4(1986) 203—212.

Primary Examiner—Thurman K. Page
Assistant Examiner—Leon R. Horne
Attorney, Agent, or Firm—Donald J. Perrella; Joseph F. DiPrima

[57] ABSTRACT

A microporous, cellulosic coating useful in combination with osmotically controlled drug delivery devices is disclosed. In one embodiment, this coating results from application to core tablets of a coating dispersion comprised of a synthetic latex formed by emulsification of cellulosic polymers stabilized by surfactants, containing a water-soluble pore forming agent and a plasticizer.

6 Claims, 4 Drawing Sheets

CELLULOSIC COATING

BACKGROUND OF THE INVENTION

1. Field of the Invention

This invention relates generally to a cellulosic coating particularly useful in combination with osmotic controlled drug delivery devices. Specifically, a cellulosic coating is combined with a pore forming agent, preferably urea, to form a microporous coating used in conjunction with an osmotically controlled drug delivery device.

2. The Prior Art

U.S. Pat. No. 4,330,338 ('338 Patent) describes pharmaceutical coatings in the form of aqueous dispersions of a water insoluble polymer, such as ethyl cellulose. In the '338 Patent, the aqueous dispersions of water-insoluble polymer are prepared by dissolving the polymer in an organic solvent more volatile than water, emulsifying the solution thus formed in a continuous water phase, and thereafter removing the organic solvent to form the latex coating. The ethyl cellulose dispersion and other coatings described in the '338 Patent provide an alternative to organic, solvent-based tablet coating formulations which suffer from environmental, safety and toxicity problems.

Tablet cores coated according to the '338 Patent release active agent by diffusion, which can be an exceedingly slow process unless systems with a large surface area are utilized. Diffusive coatings, such as those described in the '338 Patent, therefore, are most often used to coat high surface area nonpariels or beads. To expedite release of active agent from tablets coated with, e.g., an ethyl cellulose coating prepared in accordance with the disclosure of the '338 Patent, hydroxypropylmethycellulose (HPMC) has been added to the coating. HPMC, a water soluble polymer, enhances the water solubility of the ethyl cellulose coats, causing the coating and subsequently the tablet core to rapidly disintegrate in an environment of use such as the intestine. Such rapid disintegration, however, is unsuitable for those applications in which drug is to be delivered continuously over time.

U.S. Pat. No. 4,060,598 ('598 Patent) describes the use of water-soluble or alkaline-soluble materials in combination with tablet coatings made from aqueous dispersions of synthetic polymers such as polyvinyl esters, polyacrylic acid esters, polyvinyl acetals, polyvinyl chloride or butadienestyrene copolymers to ensure that the synthetic resin coating (upon exposure to an aqueous environment of use) becomes sufficiently porous to enable active agent to diffuse through the coating.

The need exists, therefore, for an organic-free tablet coating suitable for use with osmotically-controlled drug delivery devices. Ideally, this coating, upon exposure to an aqueous environment of use, would transform to a microporous state and ensure continuous release of active agent from a tablet core to that environment.

SUMMARY OF THE INVENTION

The instant invention discloses cellulosic aqueous latices containing water soluble pore forming additive(s) and plasticizer(s) that may be applied to tablet cores to form coats which become microporous in an environment of use and which provide for osmotically controlled release of the beneficial agent(s) from the core.

Coatings of the instant invention can comprise (a) polymeric cellulosic materials that are insoluble in the fluids of the environment of intended use (usually aqueous); (b) surfactants or other additives which stabilize the latex; (c) a suitable plasticizer; (d) other added excipients that will dissolve in the environmental fluids and leach out of the coats; and (e) water insoluble additives which may increase the strength of the coat or modify the tensile properties of the coat. The leached coats are porous structures comprised of numerous open and closed cells that form a discontinuous interwoven network of void spaces when viewed with a scanning electron microscope. These controlled porosity coats serve as both water entry and core composition solution exit sites.

A controlled porosity coat can be generically described as having a sponge-like appearance. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used.

The coats of the instant invention must not be covered on the inner or outer surface by a layer of material that is impermeable to dissolved solutes within the core during the period of operation.

Any cellulosic polymer permeable to water but impermeable to solutes may be used in an aqueous dispersion in a latex or pseudolatex form. The term "latex" has been traditionally defined as the viscid, milky juice secreted by the laticiferous vessels of several plants and trees. Currently, latex also refers to aqueous colloidal dispersions of natural, synthetic, or semisynthetic polymers, for example:

1. natural latices that occur as the natural products of certain plants and trees,
2. synthetic latices obtained by emulsion polymerization (i.e., latices prepared from monomers which are polymerized as an emulsion to form submicroscopic spherical polymer particles colloidally suspended in water), or
3. artificial latices which are colloidal dispersions of polymers prepared by direct emulsification of the bulk polymer in an aqueous medium. Such latices are generally stabilized by surfactants.

For industrial purposes, latices are often produced by emulsion polymerization. A monomer or mixture of monomers is emulsified in water and polymerization is induced in the aqueous phase by an initiator. Surfactants play a very important role in emulsion polymerization. Their adsorption at the interface lowers the interfacial tension between the dispersed and continuous phases and surrounds the particles with a firmly bound water envelope, stabilizing the emulsion against coagulation. The adsorbed layers of amphipathic surfactants are oriented in such a way that their hydrophilic polar heads are pointing into the continuous phase, while the hydrophobic nonpolar tails are anchored in the dispersed phase.

Other classes of polymers and resins such as the cellulosics used in the instant invention which cannot be produced as latices by emulsion polymerization may be prepared in latex form by post emulsification of the presynthesized polymer. Surfactants also play an important role in stabilization of latices made by these methods.

There are cases in which an emulsion may be prepared by the emulsification of either a polymer solution or the polymer directly, if the viscosity of the neat polymer is sufficiently low. Preparation of artificial latices by emulsification techniques can be categorized into three different basic approaches:

1. solution emulsification: the polymer is dissolved in a solvent or mixture of solvents to form a polymer solution which is immiscible with water; this solution is then emulsified in water in the presence of suitable emulsifiers and surfactants and the solvents are removed;
2. phase inversion: the polymer is first mixed with a long-chain fatty acid, and the emulsion is formed by an inversion method. When the fatty acid is thoroughly dispersed, a dilute aqueous alkali solution is slowly blended into the mixture at a temperature of approximately 100° F. The initial product is a water in polymer dispersion, but as more aqueous solution is added, an inversion of phases takes place and a dispersion of polymer particles in water is obtained; and
3. self-emulsification: the polymer molecule is chemically modified so that it becomes self-emulsifiable on dispersion in water or acids without the use of added emulsification.

Once the cellulosic polymer is in a stable aqueous dispersion, modifying additives such as plasticizers, pore forming agents and fillers may be added to alter the properties of a coating produced by application of the modified dispersion (latex) onto tablets.

Appropriate cellulosic polymers for use in the present invention include cellulose esters, cellulose mixed esters, and cellulose ethers. The glucose repeat units of the basic cellulose polymer backbone each have 3 hydroxyl groups available for derivatization. Cellulose polymers are useful in the present invention that are derivatized to the extent that 1, 2, or 3 of the hydroxyls per repeat glucose per unit are converted to ester or ether linkages. This derivatization of available hydroxyls is frequently referred to as degree of substitution, D.S., with a D.S. of 1 meaning one hydroxyl per glucose has been derivatized, D.S. of 2 meaning two hydroxyls have been derivatized, and D.S. of 3 meaning three hydroxyls have been derivatized. Non-uniform derivatization may result in fractional D.S. such as 1.9, 2.2, 2.9 and the like.

Typical of those esters that are useful in the present invention are cellulose acetates, cellulose propionates, cellulose butyrates with mixed ester cellulose derivatives such as cellulose acetate-butyrate and cellulose acetate-propionate commonly encountered. Typical of those ethers that are useful in the present invention are ethyl-cellulose. Other cellulose esters, cellulose ethers, or combinations of derivatized cellulose polymers will also work in the invention with the noted examples serving to illustrate and not restrict the scope.

Microporous cellulose coatings of the instant invention may be formed in situ by dissolution or leaching of pore formers within the coating upon exposure to an aqueous environment of use. Pores may also be formed in the coating by gas formation during curing. Pore formers useful in the present invention include water soluble compounds such as urea, dimethyl sulfone, nicotinamide, saccharides, amino acids, sorbitol, pentaerythritol, mannitol, organic aliphatic and aromatic ols, including diols and polyols, and other water soluble polymeric materials. Pores may also be formed in the wall by the volatilization of components in the polymer latex or by chemical reactions in the polymer latex which evolve gases prior to application or during application of the latex to the core tablets. A particularly preferred poreformer useful in the instant invention is urea because it is compatible with latex dispersions, nontoxic, highly water soluble, and readily leaches from the polymer to form a microporous coat.

Plasticizers can be used to lower the second-order phase transition temperature and elastic modulus of the cellulosic polymer. The workability and flexibility of the coat is increased and the fluid permeability of the coat may be either increased or decreased. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, polyethylene glycols, polypropylene glycols, and halogenated phenyls. Generally, from 0.001 to 50 parts of a plasticizer or a mixture of plasticizers are incorporated into 100 parts of wall forming material.

Flux regulators, including polyhydric alcohols and derivatives thereof, such as polyalkylene glycols can be added to the wall to increase or decrease fluid permeability. Particularly preferred flux regulators include ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid. The amount of flux regulator added to a material generally is an amount sufficient to produce the desired permeability, and it will vary according to the lamina forming material and the flux regulator used to modulate the permeability. Usually from 0.001 parts up to 50 parts, or higher of flux regulator per 100 parts coat forming material can be used to achieve the desired results.

Surfactants can be added to the coat-forming material to regulate the surface energy of the dispersed cellulosic and thereby improve the blending and dispersion of the polymer and other additives into a composite. Anionic, cationic, nonionic or amphoteric surfactants, including sulfated, sulfonated, or carboxylated esters, amides, alcohols, ethers, aromatic hydrocarbons, aliphatic hydrocarbons, acylated amino acids and peptides can be used. Examples of surfactants include potassium laurate, sodium alkylsulfates such as sodium dodecyl sulfate, hexadecylsulphonic acid, sodium dioctylsulphosuccinate, hexadecyl(cetyl)trimethylammonium bromide, dodecylpyridinium chloride, dodecylamine hydrochloride, N-dodecyl-N,N-dimethyl betaine, bile acids and salts, acacia, tragacanth, polyoxyethylated nonylphenols (Igepal), sorbitol esters (Spans), polysorbates (Tweens), polyoxyethylated toctylphenols (Triton-X analogs), polyoxyethylene lauryl ethers, polyoxyethylene cetyl ethers, polyoxyethylene stearyl ethers, polyoxyethylene oleyl ethers (Brij analogs), polyoxyethylene stearates (Myrj analogs), poloxamer and poloxamine type polyoxyethylene-polyoxypropylene derivatives (pluronics and tetronics), and surface active drug agents such as phenothiazines, tricyclic antidepressants, and the like. Suitable surfactants can be selected for blending with coat forming materials by using the surfactant's hydrophilelipophile balance number, HLB, which represents the proportion between the weight percentages of hydrophilic and lipophilic groups in a surfactant. The higher the HLB, the more hydrophilic the surfactant and the lower the number the more lipophilic the surfactant. The required HLB number for blending coat forming materials is determined by selecting a surfactant with a known HLB number, blending it with the materials and observing the results. A uniform composite is formed with the correct HLB number, while a non-uniform mixture indicates a different number is needed. This new number can be selected by using the prior HLB number as a guide. The HLB number is known to the art for many surfactants, and they can be experimentally determined. Generally a HLB number of 10 or less indicates lipophilic behavior and 10 or more indicates hydrophilic behavior. Also, HLB numbers are algebraically additive. Thus, by using a low number with a high number, blends of surfactant can be prepared having numbers intermediate between the two numbers. The concept of HLB is detailed in *Remington's Pharmaceutical Sciences,* 16th Ed., Mack Pub. Co., (1980), pages 316-319. The amount of surfactant needed is an amount that when blended with coat forming materials will form the desired coat composite, and it will vary according to the particular surfactant and materials that are blended to form the coat. Generally, the amount of surfactant will range from about 0.001 part up to 40 parts for 100 parts of coat.

Cellulosic coatings of the instant invention can also include appropriate fillers, such as those described in the "Encyclopedia of Polymer Science and Technology," John Wiley & Sons, Inc., New York: Fillers, Vol. 6, pg. 740. Suitable fillers include, but are not limited to, silicates, oxides, carbonates, sulfates, carbon and polymeric fibers.

Cellulosic coatings of the instant invention can be used to coat a core compartment comprising a solution, dispersion, paste, cream, particle, granule, emulsion, suspension or powder of drug, which can be mixed with a binder, dispersant, emulsifier or wetting agent and dyes. As used herein, the term "drug" includes any beneficial agent which is physiologically or pharmacologically active and which produces a localized or systemic effect in man or animals.

The process to produce the desired coat formulation involves the addition of the plasticizer, pore forming agent, and any other desirable additives and fillers to the cellulosic latex and mixing either magnetically or with a high shear mixer. Coating can be accomplished using a pan coater or fluidized bed apparatus. Generally, temperatures greater than 50° C. are utilized and the coating application rate can vary from 0.1 ml/min to 100 ml/min or higher. Appropriate tablet cores containing the drug are coated to the desired thickness and cured before use.

DETAILED DESCRIPTION OF A PREFERRED EMBODIMENT

Figure 1:
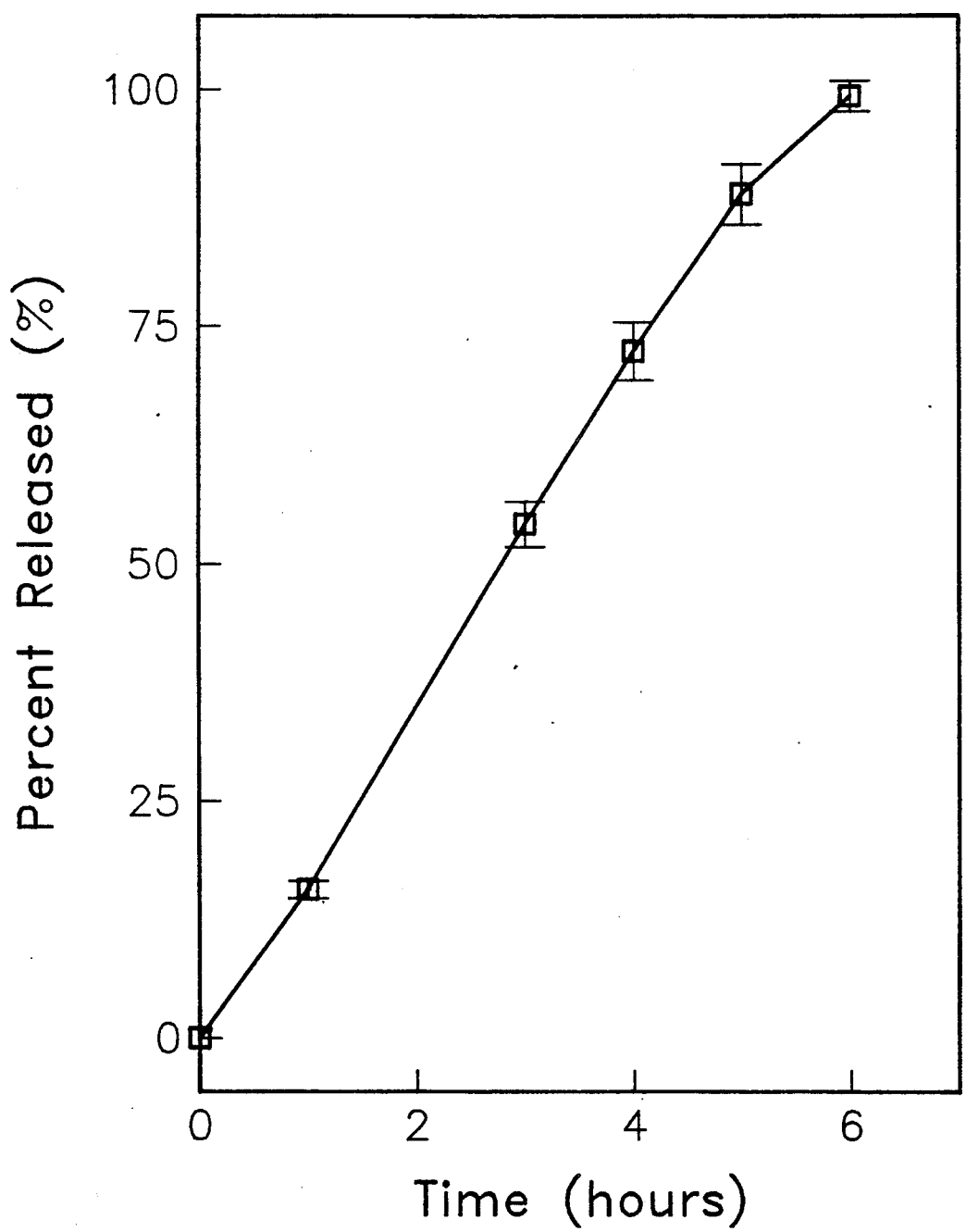
FIG. 1 illustrates a typical release profile for KCl tablets coated with a modified cellulosic latex coating (Aquacoat TM, 24% (g/g polymer) triethylcitrate, 75% (g/g polymer) urea) of the instant invention.

A preferred embodiment of the present invention is illustrated by an osmotically controlled drug delivery device with coating and core tablet specifications as follows:

A. Coating specifications. A water insoluble microporous wall surrounding a core tablet composition prepared from:
  (i) an aqueous dispersion of a cellulosic polymer that is permeable to water but substantially impermeable to solute;
  (ii) 0.1 to 100% by weight, based on the total weight of (i) and (ii), of at least one water leachable pore forming additive dispersed throughout said coat;
  (iii) 0 to 50 parts plasticizer and/or flux regulating additive per 100 parts of the combination of (i) and (ii);
  (iv) 0 to 50 parts water insoluble filler material per 100 parts of the combination of (i) and (ii); and
  (v) 0 to 40 parts surfactant per 100 parts of the combination of (i) and (ii).

B. Core Tablet Specifications. The preferred specifications for the core tablet include:
  (i) Core Drug Loading (size): 0.05 nanograms to 5 grams drug or more (includes dosage forms for humans and animals);
  (ii) Osmotic pressure developed by a solution of the core: 8 to 500 atmospheres, typically, with commonly encountered drugs and excipients; however, osmotic pressures greater than zero are acceptable;
  (iii) Core solubility: continuous, uniform release (zero-order kinetics) of 90% or greater of the initially loaded core mass is theoretically predicted if the ratio of the dissolvable core mass solubility, S, to the dissolvable core mass density, p, that is S/p, is 0.1 or lower (typically, this occurs when 10% of the initially loaded dissolvable core mass saturates a volume of external fluid equal to the total volume of the initial dissolvable core mass).

S/p ratios greater than 0.1 fall within the workings of the invention and result in lower percentages of initial core mass delivered under zero-order kinetics. S/p can be selected to give acceptable combined characteristics of stability, release rate, and manufacturability.

There is no critical upper limit as to the amount of drug that can be incorporated into a core mass, and typically the aforementioned preferred core loading will be used. The lower limit ratio of drug to excipient is dictated by the desired drug solubility, desired osmotic activity of the core composition, the desired time span and profile of release, and the pharmacological activity of the drug. Generally, the core will contain 0.01% to 90% by weight or higher, of a beneficial agent in mixture with other solute(s). Representative of compositions of matter that can be released from the device and can function as a solute are, without limitation, those compositions soluble in fluids inside the core compartment as described. Core components may be combined with excipients, binders, lubricants, glidants, and bulking agents as needed to form a core tablet suitable for application of the coat.

EXAMPLES

The following examples illustrate the preparation of drug-delivery devices using the modified cellulosic latex coatings of this invention and the controlled release of one or more therapeutically active ingredients into an environment of use.

EXAMPLE 1

Figure 2A:
FIG. 2 presents S.E.M. micrographs ($\times 1000$) of tablet coats of the instant invention prepared from a modified cellulosic latex (Aquacoat TM, 24% (g/g polymer) triethylcitrate, 75% (g/g polymer) urea) before (2A) and after (2B) immersion in water to elute the pore forming additive.
Figure 2B:
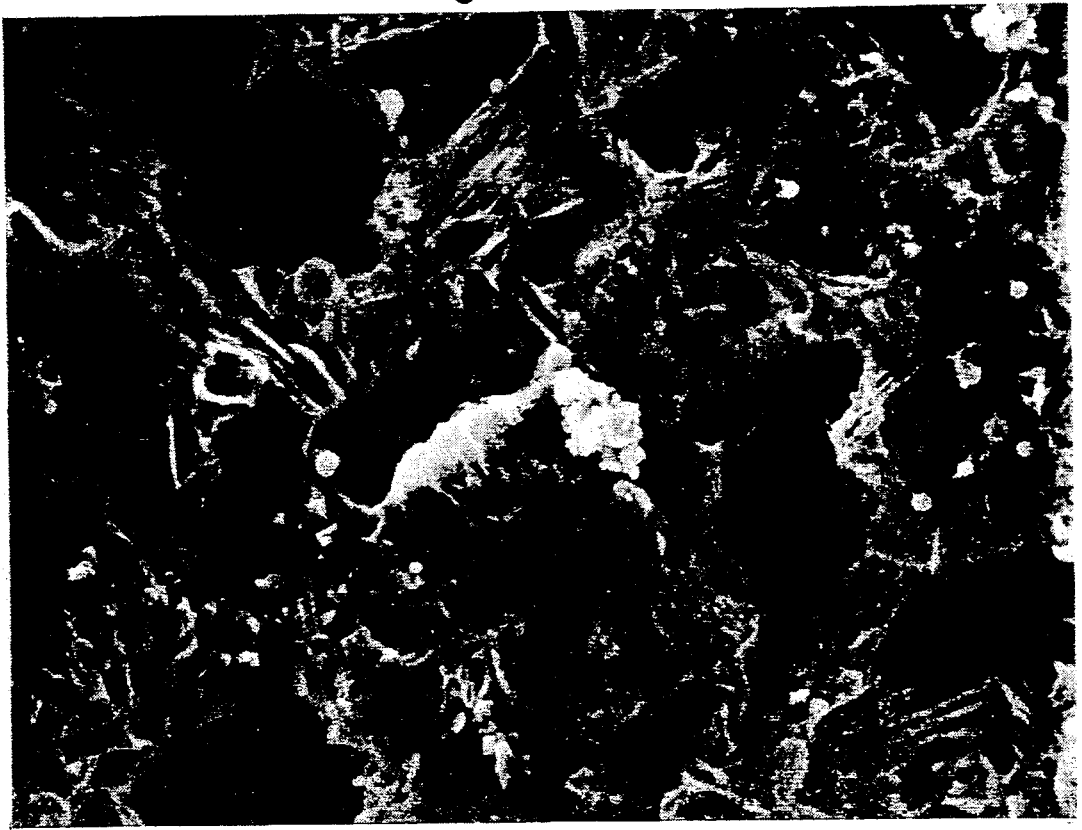

A plurality of osmotic drug delivery systems containing 500 mg potassium chloride cores were prepared. The modified latex coating formulation was prepared by adding 18 g of triethyl citrate to 250 ml of a magnetically stirred dispersion of Aquacoat TM (Aquacoat TM is an aqueous ethyl cellulose dispersion stabilized by sodium lauryl sulfate and cetyl alcohol of the type described in the aforementioned '338 Patent) followed by the addition of 56 g solid urea. This modified latex was stirred for one-half hour before use and continuously during the coating application. Coating was performed in a pan coater (Freund HCT Mini Hicoater) at a spraying rate of 1 ml/min and an inlet air temperature of 80° C. A coating 200-400 μm thick was applied. The tablets were cured at 50° C. until tested. Dissolution was performed in a standard U.S.P. dissolution method #2 apparatus in 900 ml deionized water at 37° C. with constant stirring at 50 rpm. The release of KCl was monitored by a conductivity meter (Jenway PCM3). The release profile shown in FIG. 1 shows that greater than 90% of the KCl was released with zero-order kinetics. FIG. 2 shows a scanning electron micrograph of the coating produced by this process before and after leaching. The formation of pores is clearly evident.

EXAMPLE 2

Figure 3:
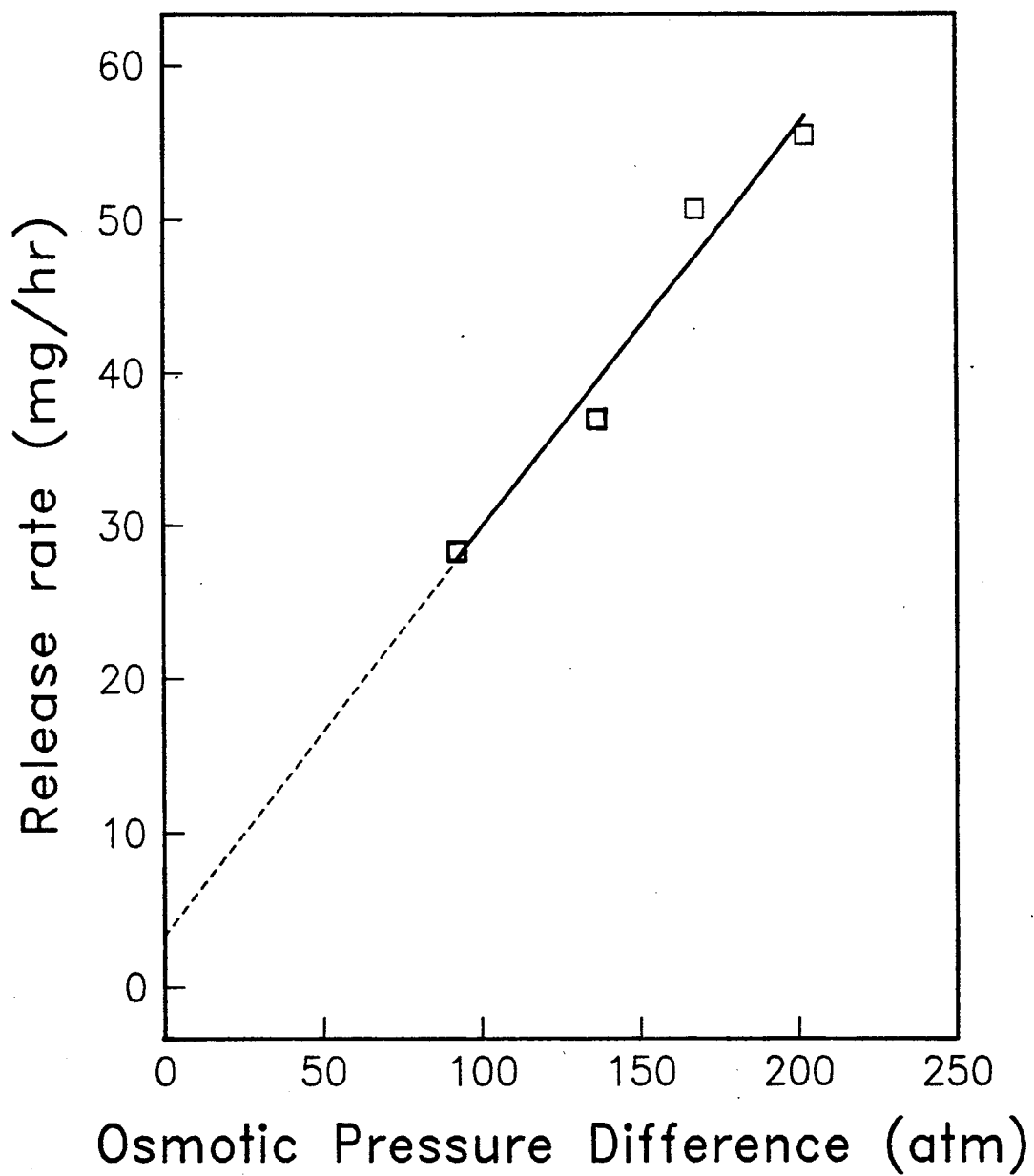
FIG. 3 illustrates the osmotic mechanism of release from a tablet coated in accordance with the instant invention.

The devices of Example 1 were used. Dissolution was performed in a standard U.S.P. dissolution method #2 apparatus in 900 ml urea solutions of various concentrations at 25° C. and 160 rpm stirring. The urea solutions were at concentrations of 1.64, 3.42, and 7.06 molal. The residual amount of KCl in devices at each time point was determined using a conductivity meter (Jenway PCM3). The relationship between the zero-order release rate and the osmotic pressure difference across the coating was summarized in FIG. 3. The linear dependence of the release rate on the osmotic pressure difference demonstrates that the release of KCl was predominantly due to an osmotic pump mechanism through the microporous wall formed from the modified cellulosic latex.

EXAMPLE 3

The cores used in this example were prepared from a granulation which contained:

| % (w/w) | Ingredient |
| --- | --- |
| 60 | diltiazem HCl |
| 14 | adipic acid |
| 12 | citric acid |
| 8 | sodium chloride |
| 5 | polyvinylpyrrolidone (29-32K) |
| 1 | stearic acid |
| 0.1 | magnesium stearate |

Figure 4:
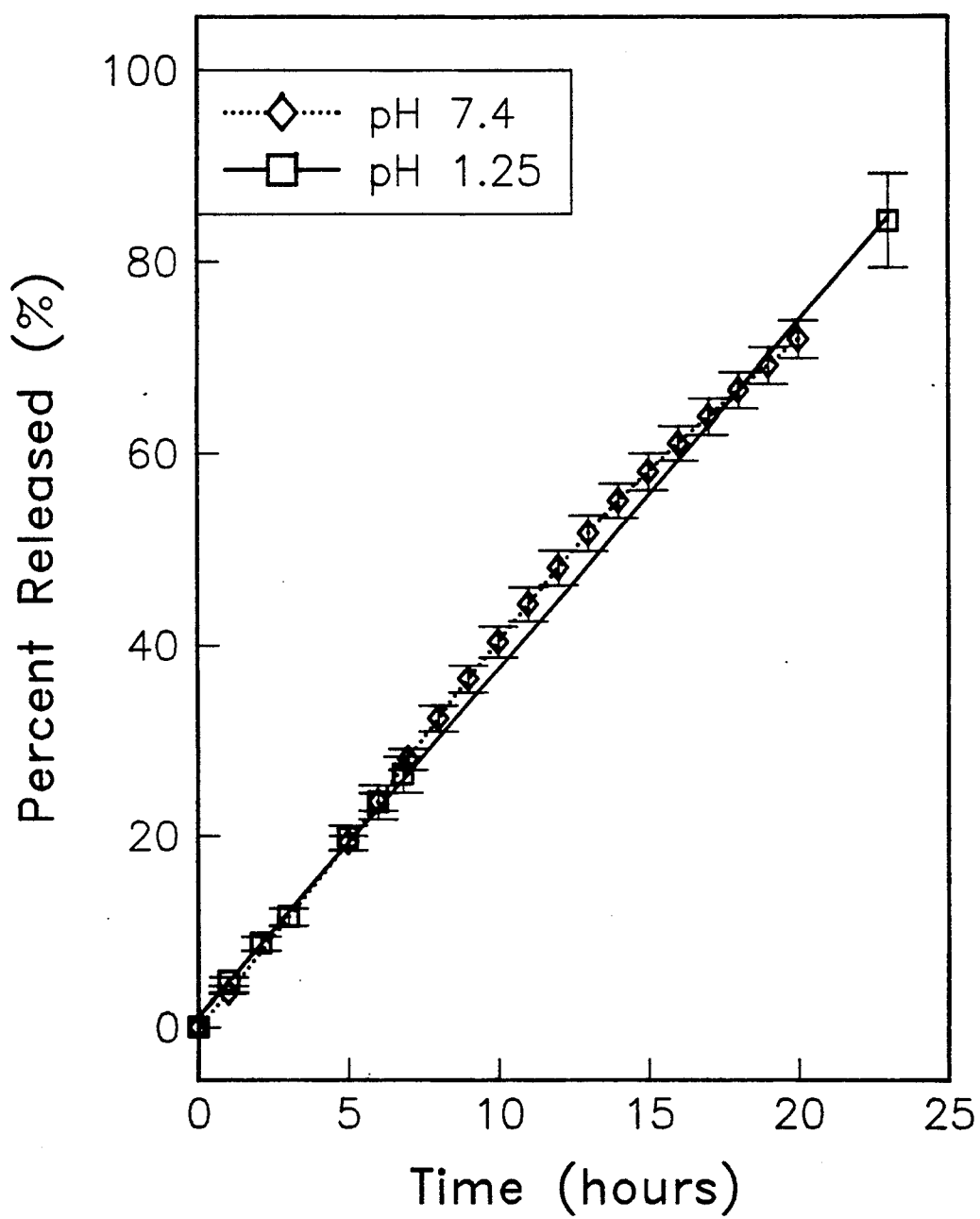
FIG. 4 illustrates typical release profiles for diltiazem·HCl tablets coated with a modified cellulosic latex (Aquacoat TM, 24% (g/g polymer) triethylcitrate, 75% (g/g polymer) urea) in accordance with the instant invention.

The granulation was tableted in a Stokes tableting machine with a 7/16" deep concave tableting die. The average tablet weight was 420 mg. The coating was as described in Example 1. Dissolution was performed in a standard U.S.P. dissolution method #2 apparatus in 900 ml aliquots of buffer at pH 1.25 or at pH 7.4 at 37° C. with constant stirring at 50 rpm. The release of diltiazem was monitored by UV at 290 nm or by HPLC using U.V. detection at 238 nm. A representative release profile is shown in FIG. 4, demonstrating 75% release at 20 hours with over 80% of the drug released with zero-order kinetics.

EXAMPLE 4

The cores and coating procedure outlined in Example 1 were used except the plasticizer was dibutyl sebacate. KCl release from this type of device with a coating thickness of 310 μm was considerably slower (6% in 6 hours).

EXAMPLE 5

The cores and coating procedure outlined in Example 1 were used except the pore former was sorbitol and the plasticizer was dibutyl sebacate. KCl release from these devices with a coating thickness of 200 μm was rapid (100% in 2 hours).

EXAMPLE 6

The cores and coating procedure outlined in Example 1 were used except the pore former was nicotinamide and the plasticizer was dibutyl sebacate. KCl release from these devices with a coating thickness of 300 μm was slow (<10% in 8 hours).

EXAMPLE 7

The cores and coating procedure outlined in Example 1 were used except the pore former was glycine and the plasticizer was dibutyl sebacate. KCl release from these devices with a coating thickness of 235 μm was slow (11% in 22 hours).

EXAMPLE 8

The cores and coating procedure outlined in Example 1 were used except Kevlar TM pulp polymeric filler was added to increase the coat strength.

EXAMPLE 9

The cores and coating procedure outlined in Example 1 were used except the urea was dissolved in water before addition to the latex.

EXAMPLE 10

The cores and coating procedure outlined in Example 1 were used except coating was accomplished using a fluidized bed coater at a temperature of 60° C. The release of KCl from these devices was slower (4%/hr) than the pan coated devices of similar thickness. The coatings of these devices were stronger than the coatings of the devices of the same thickness which were pan coated.

EXAMPLE 11

A pseudolatex is formed by dissolving cellulose acetate (10% w/w) in methanol/methylene chloride (50:50 v/v). The resulting solution is mixed with an appropriate concentration of sodium lauryl sulfate in aqueous solution under conditions of continuous high shear agitation. The resultant emulsion is ultrasonically agitated then homogenized. The organic solvent is removed under vacuum, forming a pseudo latex dispersion. This latex is used as described in Examples 1-10 as a substitute for Aquacoat ™.

What is claimed is:

1. A coating composition consisting essentially of a single layer surrounding a core compartment comprising: a latex derived from an aqueous colloidal dispersion of a cellulosic polymer, surfactant, plasticizer and a pore-forming agent selected from the group consisting of urea, dimethyl sulfone, nicotinamide, or an amino acid, which coating when first introduced into an aqueous medium is a single layer, wherein, upon exposure to water, said pore-forming agent dissolves and is eluted leaving a water-insoluble microporous cellulosic coating.

2. The coating of claim 1, further comprising at least one of the following: a flux regulator, a filler.

3. A coating of claim 1 wherein the cellulosic latex is formed by emulsification of a cellulosic polymer.

4. The coating of claim 3 further comprising at least one of the following: a flux regulator, a filler.

5. A coating of claim 3 wherein said pore-forming agent is present in an amount of 0.1 to 75 grams pore-forming agent per 100 grams of cellulosic latex.

6. The coating of claim 5 wherein said pore-forming agent is urea.

* * * * *